(12) United States Patent
Duncalf et al.

(10) Patent No.: US 7,691,873 B2
(45) Date of Patent: Apr. 6, 2010

(54) PREPARATION OF PHARMACEUTICAL FORMULATIONS

(75) Inventors: David John Duncalf, Little Neston (GB); Steven Paul Rannard, Mickle Trafford (GB); James Long, Oxton (GB); Dong Wang, Prenton (GB); Andrew James Elphick, Long Hanborough (GB); John Staniforth, Chippenham (GB); Daniele Chauvin, Chippenham (GB); Alison Jayne Foster, Higher Bebington (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 12/309,341

(22) PCT Filed: Jul. 13, 2007

(86) PCT No.: PCT/GB2007/050409

§ 371 (c)(1),
(2), (4) Date: Jan. 13, 2009

(87) PCT Pub. No.: WO2008/007152

PCT Pub. Date: Jan. 17, 2008

(65) Prior Publication Data

US 2009/0325995 A1 Dec. 31, 2009

(30) Foreign Application Priority Data

Jul. 13, 2006 (GB) .................................. 0613925.7
Jun. 29, 2007 (WO) ............... PCT/EP2007/056560

(51) Int. Cl.
*A61K 31/44* (2006.01)
*A61K 31/445* (2006.01)
(52) U.S. Cl. ....................... 514/282; 514/330
(58) Field of Classification Search .................. 514/282, 514/330
See application file for complete search history.

(56) References Cited

U.S. PATENT DOCUMENTS

| 6,207,674 B1 | 3/2001 | Smith |
| 2004/0180089 A1 | 9/2004 | Plachetka et al. |
| 2006/0105038 A1 | 5/2006 | Lai et al. |

FOREIGN PATENT DOCUMENTS

| EP | 1 598 066 A1 | 11/2005 |
| WO | WO 97/13503 A1 | 4/1997 |
| WO | WO 97/35562 A1 | 10/1997 |
| WO | WO 97/38678 A1 | 10/1997 |
| WO | WO 00/72827 A2 | 12/2000 |
| WO | WO 01/00243 A1 | 1/2001 |
| WO | WO 01/13889 A1 | 3/2001 |
| WO | WO 01/39836 A1 | 6/2001 |
| WO | WO 01/89484 A2 | 11/2001 |
| WO | WO 02/03955 A1 | 1/2002 |
| WO | WO 02/098352 A2 | 12/2002 |
| WO | WO 2004/091665 A1 | 10/2004 |
| WO | WO 2005/117837 A1 | 12/2005 |

OTHER PUBLICATIONS

Palmieri et al. (2001) "Spray-drying as a method for microparticulate controlled release systems preparation: advantages and limits. I. Water-soluable drugs." *Drug Development and Industrial Pharmacy*, 27(3): 195-204.
Raffa (2001) "Pharmacology of oral combination analgesics: Rational therapy for pain." *Journal of Clinical Pharmacy and Therapeutics*, 26(4): 257-264.
Vermeire and Remon (1999) "Compatibility and stability of ternary admixtures of morphine with haloperidol or midazolam and dexamethasone or methylprednisolone." *International Journal of Pharmaceutics*, 177(1): 53-67.
Weuts et al. (2005) "Study of the physicochemical properties and stability of solid dispersions of loperamide and PEG6000 prepared by spray drying." *European Journal of Pharmaceutics and Biopharmaceutics*, 59(1): 119-126.

*Primary Examiner*—Raymond J Henley, III
(74) *Attorney, Agent, or Firm*—Ellen Plotkin

(57) ABSTRACT

A process for the production of a composition comprising a water-insoluble opioid which comprises the steps of: a) providing a mixture comprising: i) a water-insoluble opioid, ii) a water soluble carrier, and iii) a solvent for each of the opioid and the carrier, and b) spray-drying the mixture to remove the or each solvent and obtain a substantially solvent-free nano-dispersion of the opioid in the carrier.

23 Claims, No Drawings

PREPARATION OF PHARMACEUTICAL FORMULATIONS

The subject application is a US National Stage of PCT/GB2007/050409 filed Jul. 13, 2007, and claims priority to and benefit of GB application 0613925.7 filed Jul. 13, 2006 and PCT/EP2007/056560 filed Jun. 29, 2007.

FIELD OF THE INVENTION

The present invention relates to improvements relating to pharmaceutical compositions. In particular it relates to pharmaceutically active compositions and precursors therefor which fall within the group of so-called "opioids".

BACKGROUND OF THE INVENTION

Opioids are therapeutically active agents that have a morphine-like action in the body. Their main use is as analgesics for treating moderate to severe pain, including acute pain such as post-operative pain and severe, chronic, disabling pain of terminal conditions such as cancer. They are also frequently used as anesthetics for pre-operative sedation. Some opioids are also used to treat diarrhea. In recent years there has been an increased use of opioids in the management of non-malignant chronic pain following the recognition that dependence is rare when the drug is being used for pain relief.

In addition to analgesia and anaesthesia, opioids are used to treat or prevent cough (in particular codeine, dextromethorphan and hydrocodone), to treat diarrhea, anxiety (in particular oxymorphone) and for detoxification and addiction (in particular methadone, buprenorphine, naloxone and naltrexone).

Opioids include: endogenous opioid-peptides such as endorphins, dynorphins and enkephalins; opium alkaloids such as codeine, morphine and thebaine; semisynthetic derivatives such as diacetylmorphine (heroin), dihydrocodeine, hydrocodone, hydromorphone, nicomorphine, oxycodone and oxymorphone; anilidopiperidines such as fentanyl, alphamethylfentanyl, alfentanil, sufentanil, remifentanil, carfentanyl and ohmefentanyl; phenylpiperidines such as nocaine, pethidine (meperidine), ketobemidone, MPPP, allylprodine, prodine and PEPAP; diphenylpropylamine derivatives such as propoxyphene, dextropropoxyphene, dextromoramide, bezitramide, piritramide, methadone, levoalphacetylmethadol (LAAM), loperamide and diphenoxylate; benzomorphane derivatives such as pentazocine and phenazocine; oripavine derivatives such as buprenorphine and etorphine; morphinan derivatives such as butorphanol, nalbuphine, levorphanol and levomethorphan; and other opioids such as dezocine, lefetamine, tilidine and tramadol.

Many opioids exhibit low water solubility and are practically insoluble in water. This hinders their effective use, particularly for oral delivery in base form and so water soluble salt forms are preferred, such as sulphates (e.g. morphine sulphate), citrates (e.g. fentanyl and sufentanil salts), tartrates (e.g. hydrocodone bitartrate), phosphates (e.g. codeine salt), hydrobromides (e.g. dextrometorphan salt), hydrochlorides (e.g. oxycodone, oxymorphone, hydromorphone, buprenorphine and tramadol salts).

WO 2004/011537 describes the formation of solid, porous beads comprising a three dimensional open-cell lattice of a water-soluble polymeric material. These are typically "templated" materials formed by the removal of both water and a non-aqueous dispersed phase from a high internal phase emulsion (HIPE) which has a polymer dissolved in the aqueous phase. The beads are formed by dropping the HIPE emulsion into a low temperature fluid such as liquid nitrogen, then freeze-drying the particles formed to remove the bulk of the aqueous phase and the dispersed phase. This leaves behind the polymer in the form of a "skeletal" structure. The beads dissolve rapidly in water and have the remarkable property that a water-insoluble component dispersed in the dispersed phase of the emulsion prior to freezing and drying can also be dispersed in water on solution of the polymer skeleton of the beads.

WO 2005/011636 discloses a non-emulsion based spray drying process for forming "solid amorphous dispersions" of drugs in polymers. In this method a polymer and a low-solubility drug are dissolved in a solvent and spray-dried to form dispersions in which the drug is mostly present in an amorphous form rather than in a crystalline form.

Unpublished co-pending applications (GB 0501835 of 28 Jan. 2005 and GB 0613925 filed on 13 Jul. 2006) describe how materials which will form a nano-dispersion in water can be prepared, preferably by a spray-drying process. In the first of these applications the water insoluble materials is dissolved in the solvent-phase of an emulsion. In the second, the water-insoluble materials are dissolved in a mixed solvent system and co-exist in the same phase as a water-soluble structuring agent. In both cases the liquid is dried above ambient temperature (above 20° C.), such as by spray drying, to produce particles of the structuring agent, as a carrier, with the water-insoluble materials dispersed therein. When these particles are placed in water they dissolve, forming a nano-dispersion of the water-insoluble material with particles typically below 300 nm. This scale is similar to that of virus particles, and the water-insoluble material behaves as though it were in solution.

In the present application the term "ambient temperature" means 20° C. and all percentages are percentages by weight unless otherwise specified.

BRIEF DESCRIPTION OF THE INVENTION

We have now determined that both the emulsion-based and the single-phase method can be used to produce a water-soluble, nano-disperse form of an opioid.

Accordingly, the present invention provides a process for the production of a composition comprising a water-insoluble opioid which comprises the steps of:
a) providing a mixture comprising:
   i) a water-insoluble opioid,
   ii) a water soluble carrier, and
   iii) a solvent for each of the opioid and the carrier; and
b) spray-drying the mixture to remove the or each solvent and obtain a substantially solvent-free nano-dispersion of the opioid in the carrier.

The preferred method of particle sizing for the dispersed products of the present invention employs a dynamic light scattering instrument (Nano S, manufactured by Malvern Instruments, UK). Specifically, the Malvern Instruments Nano S uses a red (633 nm) 4 mW Helium-Neon laser to illuminate a standard optical quality UV cuvette containing a suspension of material. The particle sizes quoted in this application may be obtained with that apparatus using the standard protocol. Particle sizes in solid products are the particle sizes inferred from the measurement of the particle size obtained by solution of the solid in water and measurement of the particle size.

Preferably, the peak diameter of the water-insoluble opioid is below 1500 nm. More preferably the peak diameter of the water-insoluble opioid is below 1000 nm, most preferably below 800 nm. In a particularly preferred embodiment of the invention the median diameter of the water-insoluble opioid is in the range 400 to 1000 nm, more preferably 500 to 800 nm.

Advantageous compositions obtainable by the process of the present invention comprise a water-insoluble opioid and a water soluble carrier which comprises opioid particles of 750 nm average particle size dispersed in the carrier. It is believed that reduction of the particle size in the eventual nano-dispersion has significant advantages in improving the availability of the otherwise water-insoluble material. This is believed to be particularly advantageous where an improved bio-availability is sought, or, in similar applications where high local concentrations of the material are to be avoided. Moreover it is believed that nano-dispersions with a small particle size are more stable than those with a larger particle size.

In the context of the present invention, "water insoluble" as applied to the opioid means that its solubility in water is less than 25 g/L. "Water insoluble opioids" may also mean that the solubility is less than 20 or less than 15 g/L. Preferably, the water insoluble opioid has solubility in water at ambient temperature (20° C.) less than 5 g/L preferably of less than 1 g/L, especially preferably less than 150 mg/L, even more preferably less than 100 mg/L. This solubility level provides the intended interpretation of what is meant by water-insoluble in the present specification.

Preferred water-insoluble opioids include base forms of oxycodone, hydrocodone, hydromorphone, oxymorphone, codeine, dextrometorphan, buprenorphine, morphine, fentanyl, sufentanil, alfentanil, diamorphine, morphine-6-glucuronide, noroxycodone, methadone, naloxone, nalbuphine, naltrexone, dihydrocodeine, alphamethylfentanyl, alfentanil, sufentanil, remifentanil, carfentanyl, ohmefentanyl; nocaine, pethidine (meperidine), ketobemidone, MPPP, allylprodine, prodine, PEPAP, propoxyphene, dextropropoxyphene, dextromoramide, bezitramide, piritramide, levo-alphacetylmethadol (LAAM), loperamide, diphenoxylate, pentazocine, phenazocine, etorphine, butorphanol, nalbuphine, levorphanol, levomethorphan, dezocine, lefetamine, tilidine and tramadol, and water insoluble derivatives of these compounds.

Preferred carrier materials are selected from the group consisting of water-soluble organic and inorganic materials, surfactants, polymers and mixtures thereof.

A further aspect of the present invention provides a process for preparing an opioid composition comprising a water-insoluble opioid and a water-soluble carrier, which comprises the steps of:
 a) forming an emulsion comprising:
  i) a solution of the opioid in a water-immiscible solvent for the same, and
  ii) an aqueous solution of the carrier; and
 b) drying the emulsion to remove water and the water-immiscible solvent to obtain a substantially solvent-free nano-dispersion of the opioid in the carrier.

For convenience, this class of method is referred to herein as the "emulsion" method.

A further aspect of the present invention provides a process for preparing an opioid composition comprising a water insoluble opioid and a water-soluble carrier which comprises the steps of:
 a) providing a single phase mixture comprising:
  i) at least one non-aqueous solvent,
  ii) optionally, water,
  iii) a water-soluble carrier material soluble in the mixture of (i) and (ii), and
  iv) a water-insoluble opioid which is soluble in the mixture of (i) and (ii); and
 b) drying the solution to remove water and the water miscible solvent to obtain a substantially solvent-free nano-dispersion of the opioid in the carrier.

For convenience, this class of method is referred to herein as the "single-phase" method.

In the context of the present invention substantially solvent free means within limits accepted by international pharmaceutical regulatory bodies (eg FDA, EMEA) for residual solvent levels in a pharmaceutical product and/or that the free solvent content of the product is less than 15% wt, preferably below 10% wt, more preferably below 5% wt and most preferably below 2% wt.

In the context of the present invention it is essential that both the carrier material and the opioid are essentially fully dissolved in their respective solvents prior to the drying step. It is not within the ambit of the present specification to teach the drying of slurries. For the avoidance of any doubt, it is therefore the case that the solids content of the emulsion or the mixture is such that over 90% wt, preferably over 95%, and more preferably over 98% of the soluble materials present is in solution prior to the drying step.

In relation to the methods mentioned above, the preferred opioid and the preferred carrier materials are as described above and as elaborated on in further detail below. Similarly the preferred physical characteristics of the material are as described above.

The "single phase" method where both the opioid and the carrier material are dissolved in a phase comprising at least one other non-aqueous solvent (and optional water) is preferred. This is believed to be more efficacious in obtaining a smaller particle size for the nano-disperse opioid. Preferably, the drying step simultaneously removes both the water and other solvents and, more preferably, drying is accomplished by spray drying at above ambient temperature.

The products obtainable by the process aspects of the present invention are suitable for use in the preparation of medicaments for analgesia, anaesthesia and for treating diarrhea.

A further aspect of the present invention provides a method for the preparation of a medicament for use in analgesia, anaesthesia and treating diarrhea, especially oxycodone, hydrocodone, hydromorphone, oxymorphone, codeine, dextrometorphan, buprenorphine, morphine, fentanyl, sufentanil, alfentanil, diamorphine, morphine-6-glucuronide, noroxycodone, methadone, naloxone, nalbuphine, naltrexone, dihydrocodeine, alphamethylfentanyl, alfentanil, sufentanil, remifentanil, carfentanyl, ohmefentanyl; nocaine, pethidine (meperidine), ketobemidone, MPPP, allylprodine, prodine, PEPAP, propoxyphene, dextropropoxyphene, dextromoramide, bezitramide, piritramide, levo-alphacetylmethadol (LAAM), loperamide, diphenoxylate, pentazocine, phenazocine, etorphine, butorphanol, nalbuphine, levorphanol, levomethorphan, dezocine, lefetamine, tilidine and tramadol, which comprises the step of preparing a composition according to the present invention.

DETAILED DESCRIPTION OF THE INVENTION

Various preferred features and embodiments of the present invention are described in further detail below.

Opioids

As noted above the preferred water-insoluble opioids include oxycodone, hydrocodone, hydromorphone, oxymorphone, codeine, dextrometorphan, buprenorphine, morphine, fentanyl, sufentanil, alfentanil, diamorphine, morphine-6-glucuronide, noroxycodone, methadone, naloxone, nalbuphine, naltrexone, dihydrocodeine, alphamethylfentanyl, alfentanil, sufentanil, remifentanil, carfentanyl, ohmefentanyl; nocaine, pethidine (meperidine), ketobemidone, MPPP, allylprodine, prodine, PEPAP, propoxyphene, dextropropoxyphene, dextromoramide, bezitramide, piritramide, levo-alphacetylmethadol (LAAM), loperamide, diphenoxylate, pentazocine, phenazocine, etorphine, butorphanol, nalbuphine, levorphanol, levomethorphan, dezocine, lefetamine, tilidine and tramadol and derivatives and mixtures thereof. These can be present as the sole pharmaceutically active ingredient in compositions according to the present invention or be together with other drugs to provide a so-called "combination therapy".

As an illustrative example, it would be beneficial to provide a combination of an opioid, such as oxycodone, and a further therapeutically active agent. Such further agents may also provide analgesia or anaesthesia, such as paracetamol or NSAIDs such as ibuprofen, ketoprofen, diclofenac. Alternatively, the further active agents may treat or prevent some of the adverse side effects associated with the administration of opioids. For example, nausea is one such side effect and so an opioid may be combined with an anti-emetic (e.g. low dose haloperidol). Vomiting which may be due to gastric stasis is sometimes experiences and this can be managed by combining the opioid with a prokinetic (such as domperidone or metoclopramide). Constipation develops in 99% of patients on opioids and since tolerance to this problem does not develop, nearly all patients on opioids will need a laxative and this could be provided in combination with the opioid. Oxidase inhibitors, such as quinine derivatives including quinidine and hydroquinone may be delivered in combination with opioids.

Water-Dispersible Product Form

The present invention provides a method for obtaining a water-dispersible form of an otherwise water-insoluble material. This is prepared by forming a not wholly aqueous intermediate emulsion or solution in which both a water-soluble carrier material and the water insoluble opioid are dissolved. On removal of solvents the insoluble opioid is left dispersed through the water-soluble carrier material. Suitable carrier materials are described in further detail below.

The structure of the material obtained after the drying step is not well understood. It is believed that the resulting dry materials are not encapsulates, as discrete macroscopic bodies of the water-insoluble materials are not present in the dry product. Neither are the dry materials "dry emulsions" as little or none of the volatile solvent comprising the "oil" phase of the emulsion remains after the drying step. On addition of water to the dry product the emulsion is not reformed, as it would be with a "dry emulsion". It is also believed that the compositions are not so-called solid solutions, as with the present invention the ratios of components present can be varied without loss of the benefits. Also from X-ray and DSC studies, it is believed that the compositions of the invention are not solid solutions, but comprise nano-scale, phase-separated mixtures. Further, from X-ray powder diffraction studies it is believed that the opioid nano-particle material produced is in crystalline form and not amorphous form and predominantly or entirely the same crystalline form as the starting material.

Preferably, the compositions produced after the drying step will comprise the opioid and the carrier in a weight ratio of from 1:500 to 1:1 (as opioid:carrier), 1:100 to 1:1 being preferred. Typical levels of around 10-50% wt water-insoluble opioid and 90-50% wt carrier can be obtained by spray drying.

By the method of the present invention the particle size of the opioid materials can be reduced to below 1000 nm and may be reduced to around 100 nm. Preferred particle sizes are in the range 400-800 nm.

"Emulsion" Preparation Method

In one preferred method according to the invention the solvent for the water-insoluble opioid is not miscible with water. On admixture with water it therefore can form an emulsion.

Preferably, the non-aqueous phase comprises from about 10% to about 95% v/v of the emulsion, more preferably from about 20% to about 68% v/v.

The emulsions are typically prepared under conditions which are well known to those skilled in the art, for example, by using a magnetic stirring bar, a homogeniser, or a rotational mechanical stirrer. The emulsions need not be particularly stable, provided that they do not undergo extensive phase separation prior to drying.

Homogenisation using a high-shear mixing device is a particularly preferred way to make an emulsion in which the aqueous phase is the continuous phase. It is believed that this avoidance of coarse emulsion and reduction of the droplet size of the dispersed phase of the emulsion, results in an improved dispersion of the "payload" material in the dry product.

In a preferred method according to the invention a water-continuous emulsion is prepared with an average dispersed-phase droplet size (using the Malvern peak intensity) of between 500 nm and 5000 nm. We have found that an Ultra-Turrux T25 type laboratory homogenizer (or equivalent) gives a suitable emulsion when operated for more than a minute at above 10,000 rpm.

There is a directional relation between the emulsion droplet size and the size of the particles of the payload material, which can be detected after dispersion of the materials of the invention in aqueous solution. We have determined that an increase in the speed of homogenization for precursor emulsions can decrease final particle size after re-dissolution.

It is believed that the re-dissolved particle size can be reduced by nearly one half when the homogenization speed increased from 13,500 rpm to 21,500 rpm. The homogenization time is also believed to play a role in controlling re-dissolved particle size. The particle size again decreases with increase in the homogenization time, and the particle size distribution become broader at the same time.

Sonication is also a particularly preferred way of reducing the droplet size for emulsion systems. We have found that a Hert Systems Sonicator XL operated at level 10 for two minutes is suitable.

It is believed that ratios of components which decrease the relative concentration of the opioid to the solvents and/or the carrier give a smaller particle size.

"Single Phase" Preparation Method

In an alternative method according to the present invention both the carrier and the opioid are soluble in a non-aqueous solvent or a mixture of such a solvent with water. Both here and elsewhere in the specification the non-aqueous solvent can be a mixture of non-aqueous solvents.

In this case the feedstock of the drying step can be a single phase material in which both the water-soluble carrier and the water-insoluble opioid are dissolved. It is also possible for this feedstock to be an emulsion, provided that both the carrier and the opioid are dissolved in the same phase.

The "single-phase" method is generally believed to give a better nano-dispersion with a smaller particle size than the emulsion method.

It is believed that ratios of components which decrease the relative concentration of the opioid to the solvents and/or the carrier give a smaller particle size.

Drying

Spray drying is well known to those versed in the art. In the case of the present invention some care must be taken due to the presence of a volatile non-aqueous solvent in the emulsion being dried. In order to reduce the risk of explosion when a flammable solvent is being used, an inert gas, for example nitrogen, can be employed as the drying medium in a so-called closed spray-drying system. The solvent can be recovered and re-used.

We have found that the Buchi B-290 type laboratory spray drying apparatus is suitable.

It is preferable that the drying temperature should be at or above 100 Celsius, preferably above 120° C. and most preferably above 140° C. Elevated drying temperatures have been found to give smaller particles in the re-dissolved nano-disperse material.

Carrier Material

The carrier material is water soluble, which includes the formation of structured aqueous phases as well as true ionic solution of molecularly mono-disperse species. The carrier material preferably comprises an inorganic material, surfactant, a polymer or may be a mixture of two or more of these.

It is envisaged that other non-polymeric, organic, water-soluble materials such as sugars can be used as the carrier. However the carrier materials specifically mentioned herein are preferred.

Suitable carrier materials (referred to herein as "water soluble carrier materials") include preferred water-soluble polymers, preferred water-soluble surfactants and preferred water-soluble inorganic materials.

Preferred Polymeric Carrier Materials

Examples of suitable water-soluble polymeric carrier materials include:

(a) natural polymers (for example naturally occurring gums such as guar gum, alginate, locust bean gum or a polysaccharide such as dextran;

(b) cellulose derivatives for example xanthan gum, xyloglucan, cellulose acetate, methylcellulose, methyl-ethylcellulose, hydroxy-ethylcellulose, hydroxy-ethylmethyl-cellulose, hydroxy-propylcellulose, hydroxy-propylmethylcellulose, hydroxy-propylbutylcellulose, ethylhydroxy-ethylcellulose, carboxy-methylcellulose and its salts (e.g. the sodium salt—SCMC), or carboxy-methylhydroxyethylcellulose and its salts (for example the sodium salt);

(c) homopolymers of or copolymers prepared from two or more monomers selected from: vinyl alcohol, acrylic acid, methacrylic acid, acrylamide, methacrylamide, acrylamide methylpropane sulphonates, aminoalkylacrylates, aminoalkyl-methacrylates, hydroxyethylacrylate, hydroxyethylmethylacrylate, vinyl pyrrolidone, vinyl imidazole, vinyl amines, vinyl pyridine, ethyleneglycol and other alkylene glycols, ethylene oxide and other alkylene oxides, ethyleneimine, styrenesulphonates, ethyleneglycolacrylates and ethyleneglycol methacrylate;

(d) cyclodextrins, for example β-cyclodextrin; and (e) mixtures thereof.

When the polymeric material is a copolymer it may be a statistical copolymer (heretofore also known as a random copolymer), a block copolymer, a graft copolymer or a hyper-branched copolymer. Co-monomers other than those listed above may also be included in addition to those listed if their presence does not destroy the water soluble or water dispersible nature of the resulting polymeric material.

Examples of suitable and preferred homopolymers include poly-vinylalcohol, poly-acrylic acid, poly-methacrylic acid, poly-acrylamides (such as poly-N-isopropylacrylamide), poly-methacrylamide; poly-acrylamines, poly-methyl-acrylamines, (such as polydimethylaminoethylmethacrylate and poly-N-morpholinoethylmethacrylate), polyvinylpyrrolidone, poly-styrenesulphonate, polyvinylimidazole, polyvinylpyridine, poly-2-ethyl-oxazoline poly-ethyleneimine and ethoxylated derivatives thereof.

Polyethylene glycol (PEG), polyvinylpyrrolidone (PVP), poly(2-ethyl-2-oxazaline), polyvinyl alcohol (PVA) hydroxypropyl cellulose and hydroxypropyl-methyl cellulose (HPMC) and alginates are preferred polymeric carrier materials.

Preferred Surfactant Carrier Materials

Where the carrier material is a surfactant, the surfactant may be non-ionic, anionic, cationic, amphoteric or zwitterionic.

Examples of suitable non-ionic surfactants include ethoxylated triglycerides; fatty alcohol ethoxylates; alkylphenol ethoxylates; fatty acid ethoxylates; fatty amide ethoxylates; fatty amine ethoxylates; sorbitan alkanoates; ethylated sorbitan alkanoates; alkyl ethoxylates; Pluronics™; alkyl polyglucosides; stearol ethoxylates; and alkyl polyglycosides.

Examples of suitable anionic surfactants include alkylether sulfates; alkylether carboxylates; alkylbenzene sulfonates; alkylether phosphates; dialkyl sulfosuccinates; sarcosinates; alkyl sulfonates; soaps; alkyl sulfates; alkyl carboxylates; alkyl phosphates; paraffin sulfonates; secondary n-alkane sulfonates; alpha-olefin sulfonates; and isethionate sulfonates.

Examples of suitable cationic surfactants include fatty amine salts; fatty diamine salts; quaternary ammonium compounds; phosphonium surfactants; sulfonium surfactants; and sulfonxonium surfactants.

Examples of suitable zwitterionic surfactants include N-alkyl derivatives of amino acids (such as glycine, betaine, aminopropionic acid); imidazoline surfactants; amine oxides; and amidobetaines.

Mixtures of surfactants may be used. In such mixtures there may be individual components which are liquid, provided that the carrier material overall, is a solid.

Alkoxylated nonionics (especially the PEG/PPG Pluronic™ materials), phenol-ethoxylates (especially TRITON™ materials), alkyl sulphonates (especially SDS), ester surfactants (preferably sorbitan esters of the Span™ and Tween™ types) and cationics (especially cetyltrimethylammonium bromide—CTAB) are particularly preferred as surfactant carrier materials.

Preferred Inorganic Carrier Materials

The carrier material can also be a water-soluble inorganic material which is neither a surfactant nor a polymer. Simple organic salts have been found suitable, particularly in admixture with polymeric and/or surfactant carrier materials as described above. Suitable salts include carbonate, bicarbonates, halides, sulphates, nitrates and acetates, particularly soluble salts of sodium, potassium and magnesium. Preferred materials include sodium carbonate, sodium bicarbonate and sodium sulphate. These materials have the advantage that they are cheap and physiologically acceptable. They are also relatively inert as well as compatible with many materials found in pharmaceutical products.

Mixtures of carrier materials are advantageous. Preferred mixtures include combinations of surfactants and polymers, which include at least one of:

a) polyethylene glycol (PEG), polyvinylpyrrolidone (PVP), hydroxypropyl cellulose and hydroxypropyl-methyl cellulose (HPMC), and alginates;

and at least one of:

b) alkoxylated nonionics (especially the PEG/PPG Pluronic™ materials), phenol-ethoxylates (especially TRITON™ materials), alkyl sulphonates (especially SDS), ester surfactants (preferably sorbitan esters of the Span™ and Tween™ types) and cationics (especially cetyltrimethylammonium bromide—CTAB).

The carrier material can also be a water-soluble small organic material which is neither a surfactant, a polymer nor an inorganic carrier material. Simple organic sugars have been found to be suitable, particularly in admixture with a polymeric and/or surfactant carrier material as described above. Suitable small organic materials include mannitol, polydextrose, xylitol, maltitol, dextrose, dextrins, dextrans, maltodextrin and inulin, etc.

Non-Aqueous Solvent The compositions of the invention comprise a volatile, second non-aqueous solvent. This may either be miscible with the other solvents in pre-mix before drying or, together with those solvents may form an emulsion.

In one alternative form of the invention a single, non-aqueous solvent is employed in which can form a single phase with water in the presence of the opioid and the carrier. Preferred solvents for these embodiments are polar, protic or aprotic solvents. Generally preferred solvents have a dipole moment greater than 1 and a dielectric constant greater than 4.5.

Particularly preferred solvents are selected from the group consisting of haloforms (preferably dichloromethane, chloroform), lower (C1-C10) alcohols (preferably methanol, ethanol, isopropanol, isobutanol), organic acids (preferably formic acid, acetic acid), amides (preferably formamide, N,N-dimethylformamide), nitriles (preferably aceto-nitrile), esters (preferably ethyl acetate) aldehydes and ketones (preferably methyl ethyl ketone, acetone), and other water miscible species comprising heteroatom bond with a suitably large dipole (preferably tetrahydrofuran, dialkylsulphoxide).

Haloforms, lower alcohols, ketones and dialkylsulphoxides are the most preferred solvents.

In another alternative form of the invention the non-aqueous solvent is not miscible with water and forms an emulsion.

The non-aqueous phase of the emulsion is preferably selected from one or more from the following group of volatile organic solvents:

alkanes, preferably heptane, n-hexane, isooctane, dodecane, decane;

cyclic hydrocarbons, preferably toluene, xylene, cyclohexane;

halogenated alkanes, preferably dichloromethane, dichoroethane, trichloromethane (chloroform), fluorotrichloromethane and tetrachloroethane;

esters, preferably ethyl acetate;

ketones, preferably 2-butanone;

ethers, preferably diethyl ether;

volatile cyclic silicones, preferably either linear or cyclomethicones containing from 4 to 6 silicon units. Suitable examples include DC245 and DC345, both of which are available from Dow Corning Inc.

Preferred solvents include dichloromethane, chloroform, ethanol, acetone and dimethyl sulphoxide.

Preferred non-aqueous solvents, whether miscible or not, have a boiling point of less than 150° C. and, more preferably, have a boiling point of less than 100° C., so as to facilitate drying, particularly spray-drying under practical conditions and without use of specialised equipment. Preferably they are non-flammable, or have a flash point above the temperatures encountered in the method of the invention.

Preferably, the non-aqueous solvent comprises from about 10% to about 95% v/v of any emulsion formed, more preferably from about 20% to about 80% v/v. In the single phase method the level of solvent is preferably 20-100% v/v.

Particularly preferred solvents are alcohols, particularly ethanol and halogenated solvents, more preferably chlorine-containing solvents, most preferably solvents selected from (di- or trichloromethane).

Optional Cosurfactant

In addition to the non-aqueous solvent an optional co-surfactant may be employed in the composition prior to the drying step. We have determined that the addition of a relatively small quantity of a volatile cosurfactant reduced the particle diameter of the material produced. This can have a significant impact on particle volume. For example, reduction from 297 nm to 252 nm corresponds to a particle size reduction of approximately 40%. Thus, the addition of a small quantity of co-surfactant offers a simple and inexpensive method for reducing the particle size of materials according to the present invention without changing the final product formulation.

Preferred co-surfactants are short chain alcohols or amine with a boiling point of <220° C.

Preferred co-surfactants are linear alcohols. Preferred co-surfactants are primary alcohols and amines. Particularly preferred co-surfactants are selected from the group consisting of the 3-6 carbon alcohols. Suitable alcohol co-surfactants include n-propanol, n-butanol, n-pentanol, n-hexanol, hexylamine and mixtures thereof.

Preferably the co-surfactant is present in a quantity (by volume) less than the solvent preferably the volume ratio between the solvent and the co-surfactant falls in the range 100:40 to 100:2, more preferably 100:30 to 100:5.

Preferred Spray-Drying Feedstocks

Typical spray drying feedstocks comprise:

a) a surfactant;

b) at least one lower alcohol;

c) more than 0.1% of at least one water-insoluble opioid dissolved in the feedstock;

d) a polymer; and, e) optional water.

Preferred spray-drying feedstocks comprise:

a) at least one non-aqueous solvent selected from dichloromethane, chloroform, ethanol, acetone, and mixtures thereof;

b) a surfactant selected from PEG co-polymer nonionics (especially the PEG/PPG Pluronic™ materials), alkyl sulphonates (especially SDS), ester surfactants (preferably sorbitan esters of the Span™ and Tween™ types) and cationics (especially cetyltrimethylammonium bromide—CTAB) and mixtures thereof;

c) more than 0.1% of at least one water-insoluble opioid;

d) a polymer selected from Polyethylene glycol (PEG), Polyvinyl alcohol (PVA), polyvinyl-pyrrolidone (PVP), hydroxypropyl cellulose and hydroxypropyl-methyl cellulose (HPMC), alginates and mixtures thereof; and e) optionally, water.

The drying feed-stocks used in the present invention are either emulsions or solutions which preferably do not contain any solid matter and in particular preferably do not contain any undissolved opioid.

The level of the opioid in the composition may be up to 95% wt, up to 90%, up to 85%, up to 80%, up to 75%, up to 70%, up to 65%, up to 60%, up to 55%, up to 50%, up to 45%, up to 40%, up to 35% or up to 30%. It is particularly preferable that the level of the opioid in the composition should be such that the loading in the dried composition is below 400% wt, and more preferably below 30% wt. Such compositions have the advantages of a small particle size and high effectiveness as discussed above.

Water-Dispersed Form

On admixture of the water-soluble carrier material with water, the carrier dissolves and the water-insoluble opioid is dispersed through the water in sufficiently fine form that it behaves like a soluble material in many respects. The particle size of the water-insoluble materials in the dry product is preferably such that, on solution in water the water-insoluble materials have a particle size of less than 1 μm as determined by the Malvern method described herein. It is believed that there is no significant reduction of particle size for the opioid on dispersion of the solid form in water.

By applying the present invention significant levels of "water-insoluble" materials can be brought into a state which is largely equivalent to true solution. When the dry product is dissolved in water it is possible to achieve optically clear solutions comprising more than 0.1%, preferably more than 0.5% and more preferably more than 1% of the water-insoluble material.

It is envisaged that the solution form will be a form suitable for administration to a patient either "as is" or following further dilution. In the alternative, the solution form of embodiments of the invention may be combined with other active materials to yield a medicament suitable for use in combination therapy.

EXAMPLES

In order that the present invention may be further understood and carried forth into practice it is further described below with reference to non-limiting examples.

A range of formulations were produced based on different excipients and different loadings of excipients, with 40% of drug in each of them. The drug used was oxycodone base (Macfarlane Smith Ltd, Edinburgh).

The excipients were chosen from hydroxypropylmethylcellulose (HPMC 5 cps viscosity grade—Methocel E5, Colorcon Ltd), Maltitol (Maltisorb P90, Roquette Ltd), Polydextran (Litesse II, Danisco Ltd), polyvinylpyrrolidone (PVP K30 grade, ISP), polysorbate 80 (Tween 80, Merck), poloxamer (Pluronic F127 grade, BASF), mannitol (Mannogem EZ) and Sodium lauryl sulphate (Fluka).

The spray drying temperature used in all examples was 100° C. and the atomisation pressure was 3.5 bar. The median volume diameters of the composite particles containing oxycodone were in the range 2,187 μm to 3,295 μm.

Details of these formulations are listed as below:

Example 1

Non Ionic Surfactants Mixture 1.8208 g oxycodone was left to stir with a magnetic bar in 657 mL of ethanol for 90 minutes. 1.640 g HPMC was added to this ethanolic solution and left to stir with a magnetic bar for 1 hour. Separately, an aqueous solution was prepared by adding 0.273 g Maltitol, 0.273 g Polydextran, 0.273 g Pluronic F127 and 0.273 g Tween 80 to 144 mL water and was left to stir with a magnetic bar for about 20 minutes. Then the aqueous solution was added to the ethanolic oxycodone solution and left to stir for about half hour.

The solution was then spray dried with a BUCHI Mini B-290 spray dryer at 100° C. with the liquid feed rate at 2.326 ml/min. A white free flowing powder was obtained.

Particle size measurement using a Malvern Mastersizer 2000 showed the $d_{(0.5)}$ to be 2.665 μm.

Example 2

High HPMC and High Polysorbate Content 2.003 g Oxycodone left to stir with a magnetic bar in 700 mL of ethanol for 90 minutes. 1.80 g HPMC was added to this ethanolic solution and left to stir with a magnetic bar for 1 hour. Separately, an aqueous solution was prepared by adding 0.3 g Maltitol, 0.3 g Polydextran and 0.6 g Tween 80 to 158 mL water and was left to stir with a magnetic bar for about 20 minutes. Then the aqueous solution was added to the ethanolic oxycodone solution and left to stir for about half hour.

The solution was then spray dried with a BUCHI Mini B-290 spray dryer at 100° C. with the liquid feed rate at 2.028 ml/min. A white free flowing powder was obtained.

Particle size measurement using a Malvern Mastersizer 2000 showed the $d_{(0.5)}$ to be 2.187 μm.

Example 3

Ionic Surfactant/High Polyol Content 2.008 g Oxycodone was left to stir with a magnetic bar in 700 mL of ethanol for 90 minutes. 1.20 g HPMC was added to this ethanolic solution and left to stir with a magnetic bar for 1 hour. Separately, an aqueous solution was prepared by adding 0.1 g SLS and 1.7 g Manitol to 158 mL water and was left to stir with a magnetic bar for about 20 minutes. Then the aqueous solution was added to the ethanolic oxycodone solution and left to stir for about half hour.

The solution was then spray dried with a BUCHI Mini B-290 spray dryer at 100° C. with the liquid feed rate at 2.5 ml/min. A white free flowing powder was obtained.

Particle size measurement using a Malvern Mastersizer 2000 showed the $d_{(0.5)}$ to be 2.906 μm.

Example 4

1.80 g PVP left to stir with a magnetic bar into 700 mL ethanol for 20 min until fully dissolved. 2.00 g Oxycodone was added to the ethanolic solution and left to stir with a magnetic bar for 2 hours. Separately an aqueous solution was prepared by adding 0.3 g Maltitol, 0.3 g Pluronic F127, 0.300 g Polydextran and 0.3 g Tween 80 to 158 mL water and was left to stir with a magnetic bar for about 20 minutes. Then the aqueous solution was added to the ethanolic oxycodone solution and left to stir for about half hour.

The solution was then spray dried with a BUCHI Mini B-290 spray dryer at 100° C. with the liquid feed rate at 2.47 ml/min. A white free flowing powder was obtained.

Particle size measurement using a Malvern Mastersizer 2000 showed the $d_{(0.5)}$ to be 3.295 μm.

Example 5

2.00 g Oxycodone left to stir with a magnetic bar in 700 mL of ethanol for 90 minutes. 1.50 g HPMC and 0.5 g PVP K30 was added to this ethanolic solution and left to stir with a magnetic bar for 1 hour. Separately, an aqueous solution was prepared by adding 0.3 g Maltitol, 0.3 g Polydextran and 0.6 g Tween 80 to 158 mL water and was left to stir with a magnetic bar for about 20 minutes. Then the aqueous solution was added to the ethanolic oxycodone solution and left to stir for about half hour.

The solution was then spray dried with a BUCHI Mini B-290 spray dryer at 100° C. with the liquid feed rate at 2.384 ml/min. A white free flowing powder was obtained.

Particle size measurement using a Malvern Mastersizer 2000 showed the $d_{(0.5)}$ to be 2.499 µm.

It has been shown that 90% of the drug dissolves within 5 minutes using a Type II USP dissolution apparatus using 0.1M HCl.

The invention claimed is:

1. A process for the production of a composition comprising a water-insoluble opioid which comprises the steps of:
   a) providing a mixture comprising:
      i) a water-insoluble opioid,
      ii) a water soluble carrier, and
      iii) a solvent for each of the opioid and the carrier; and
   b) spray-drying the mixture to remove the or each solvent and obtain a substantially solvent-free nano-dispersion of the opioid in the carrier.

2. A process according to claim 1, which comprises the steps of:
   a) providing an emulsion comprising:
      i) a solution of the opioid in a water-immiscible solvent for the same, and
      ii) an aqueous solution of the carrier; and
   b) spray-drying the emulsion to remove water and the water-immiscible solvent to obtain a substantially solvent-free nano-dispersion of the opioid in the carrier.

3. A process according to claim 1, which comprises the steps of:
   a) providing a single phase mixture comprising:
      i) at least one non-aqueous solvent,
      ii) optionally, water,
      iii) a water-soluble carrier material soluble in the mixture of (i) and (ii), and
      iv) a water-insoluble opioid which is soluble in the mixture of (i) and (ii); and
   b) spray-drying the solution to remove water and the water miscible solvent to obtain a substantially solvent-free nano-dispersion of the opioid in the carrier.

4. A process according to claim 1, wherein the spray drying process is conducted at a temperature at or above 120° C.

5. A process according to claim 1, in which the carrier material includes a polymer and/or a surfactant.

6. A process according to claim 5, wherein the carrier material includes at least one of polyethylene glycol, polyvinylpyrrolidone, poly(2-ethyl-2-oxazaline), polyvinyl alcohol, hydroxypropyl cellulose and hydroxypropyl-methyl cellulose and alginate.

7. A process according to claim 5, wherein the carrier material includes at least one of alkoxylated non-ionic surfactant, ether sulphate surfactant, cationic surfactant or ester surfactant.

8. A process according to claim 1, wherein the non-aqueous solvent includes at least one of dichloromethane, chloroform, ethanol, acetone and dimethyl sulphoxide.

9. A process for the preparation of a medicament for use in analgesia, anaesthesia or treating diarrhea, which comprises the step of preparing a composition by a process according to claim 1.

10. A composition comprising a water-insoluble opioid and a water soluble carrier which comprises opioid particles with an average particle size of between 100 and 1500 nm dispersed in the carrier.

11. A composition according to claim 10, wherein the composition is obtained or obtainable by a process comprising
   a) providing a single phase mixture comprising:
      i) at least one non-aqueous solvent,
      ii) optionally, water,
      iii) a water-soluble carrier material soluble in the mixture of (i) and (ii), and
      iv) a water-insoluble opioid which is soluble in the mixture of (i) and (ii); and
   b) spray-drying the solution to remove water and the water miscible solvent to obtain a substantially solvent-free nano-dispersion of the opioid in the carrier.

12. A composition according to claim 10, wherein the average particle size of the opioid particles is between 200 and 1000 nm, 400 and 1000 nm or 500 and 800 nm.

13. A composition according to claim 10, wherein the opioid particles are substantially crystalline.

14. A composition according to claim 10, wherein the opioid particles retain the crystallinity of the original triptan material used to prepare the composition.

15. A composition according to claim 10, wherein the opioid particles are substantially free of amorphous material.

16. A composition according to claim 10, further comprising one or more further therapeutically active agent.

17. A composition according to claim 16, wherein the composition comprises an analgesic agent, paracetamol or an NSAID.

18. A composition according to claim 16, wherein the composition comprises an anti-nausea agent, or haloperidol.

19. A composition according to claim 16, wherein the composition comprises a prokinetic, domperidone or metoclopramine.

20. A composition according to claim 16, wherein the composition comprises a laxative.

21. A composition according to claim 16, wherein the composition comprises an oxidase inhibitor, or a quinine derivative.

22. A composition according to claim 10, for use in analgesia, anaesthesia or treating diarrhea.

23. A method of providing analgesia, anaesthesia or treating diarrhea, comprising administering to a patient a therapeutically effective amount of a composition according to claim 10.

* * * * *